United States Patent [19]

Mizogami et al.

[11] Patent Number: 4,607,034

[45] Date of Patent: Aug. 19, 1986

[54] QUINAZOLINE DERIVATIVES AND PHARMACEUTICAL COMPOSITION THEREOF

[75] Inventors: Susumu Mizogami; Hidetoshi Hiranuma, both of Amimachi; Tetsuo Sekiya, Ibaraki; Mitsuo Hanazuka, Amimachi, all of Japan

[73] Assignee: Mitsubishi Yuka Pharmaceutical Co., Ltd., Tokyo, Japan

[21] Appl. No.: 199,565

[22] Filed: Oct. 21, 1980

[30] Foreign Application Priority Data

Oct. 29, 1979 [JP] Japan ................. 54-138727
Nov. 28, 1979 [JP] Japan ................. 54-152910

[51] Int. Cl.[4] ............... A61K 31/505; C07D 403/04
[52] U.S. Cl. ........................ 514/254; 514/218; 544/291
[58] Field of Search .............. 544/291; 424/251; 260/243.3; 514/218, 254

[56] References Cited

U.S. PATENT DOCUMENTS

| 3,635,979 | 1/1972 | Hess | 544/291 |
|---|---|---|---|
| 4,001,237 | 1/1977 | Partyka et al. | 544/291 |
| 4,062,844 | 12/1977 | Hammen | 544/291 |
| 4,243,666 | 1/1981 | Campbell et al. | 544/291 |
| 4,287,341 | 9/1981 | Hess et al. | 544/291 |

FOREIGN PATENT DOCUMENTS

| 57-156467 | 9/1982 | Japan | 544/291 |
|---|---|---|---|
| 59-29674 | 2/1984 | Japan | 544/291 |

OTHER PUBLICATIONS

Sekiya et al., Pyrimidine derivatives 1. Eur. J. Med. Chem.—Chimica Therapeutica, Jul.-Aug. 1980-15, No. 4, pp. 317–322.

Primary Examiner—Glennon H. Hollrah
Assistant Examiner—James H. Turnipseed
Attorney, Agent, or Firm—Frishauf, Holtz, Goodman & Woodward

[57] ABSTRACT

There are presented novel quinazoline derivatives, namely 2-(4-substituted-carbamoyl-piperazin-1-yl)quinazoline derivatives, 2-(4-substituted-carbamoyl-homopiperazin-1-yl)quinazoline derivatives, 2-(4-substituted-thiocarbamoyl-piperazin-1-yl)quinazoline derivatives and 2-(4-substituted-thiocarbamoyl-piperazin-1-yl)quinazoline derivatives, having excellent antihypertensive activities.

22 Claims, No Drawings

QUINAZOLINE DERIVATIVES AND PHARMACEUTICAL COMPOSITION THEREOF

This invention relates to novel quinazoline derivatives. More particularly, the present invention pertains to 2-(4-substituted-carbamoyl-piperazin-1-yl)quinazoline derivatives, 2-(4-substituted-carbamoyl-homopiperazin-1-yl)quinazoline derivatives, 2-(4-substituted-thiocarbamoyl-piperazin-1-yl)quinazoline derivatives and 2-(4-substituted-thiocarbamoyl-homopiperazin-1-yl)quinazoline derivatives, having antihypertensive activities.

As a quinazoline type antihypertensive, there may be mentioned a compound widely known under the name of "prazosin", as disclosed in U.S. Pat. No. 3,511,836. Said prazosin is 2-[4-(2-furoyl)-piperazin-1-yl]-4-amino-6,7-dimethoxyquinazoline having the following formula (A):

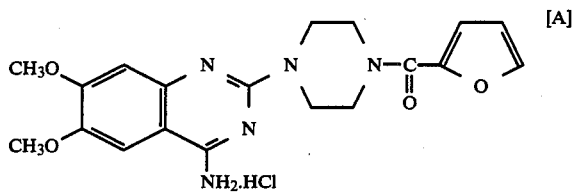

The antihypertensive activity of said compound is known to be based on relaxation of peripheral arterioles as a consequence of α-adrenoceptor blockade. As the alternative compounds having antihypertensive activities analogous to prazosin, there have been known the compounds wherein the furyl group in the above formula (A) is substituted by such a group as a phenyl group, a thienyl group, an alkoxy group, a tetrahydrofuryl group, a tetrahydropyranyl group, a cycloalkyl group, a thiazyl group (thiazolyl group), a substituted-oxadiazolyl group, etc.; the compounds represented by the following formula (B):

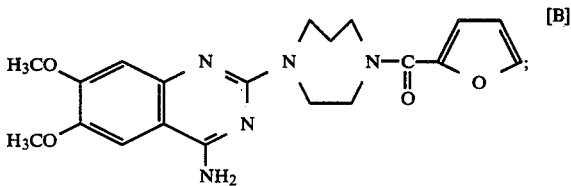

and the compounds wherein the furyl group in the formula [B] is substituted by such a group as a substituted-phenylvinyl group, a substituted phenyl group, a tetrahydrofuryl group, a tetrahydropyranyl group, etc., as disclosed in, for example, Japanese Patent Publication No. 45(1970)-22135, Japanese Provisional Patent Publications Nos. 51(1976)-80877, 50(1975)-93987, 49(1974)-66690, 49(1974)-66691, 52(1977)-100479, 50(1975)-140474, 5181976)-82285, 52(1977)-48678, 52(1977)-48681 and 52(1977)-102286. Further, British Pat. No. 1,156,973 discloses a compound having antihypertensive activity in which the furoyl group:

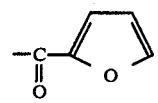

is substituted by a substituted- or unsubstituted-carbamoyl group represented by the following formula [C]:

wherein $R_m$ and $R_n$ each represent a hydrogen atom or an alkyl group having 1 to 6 carbon atoms.

The present inventors have sought after the compounds having further improved activities in view of the quinazoline derivatives having antihypertensive activities known from these prior arts, and consequently discovered novel quinazoline derivatives to accomplish the present invention.

The object of the present invention is to provide novel and useful quinazoline derivatives.

The novel quinazoline derivatives according to the present invention are quinazoline derivatives or pharmaceutically acceptable acid addition salts thereof represented by the following formula [I]

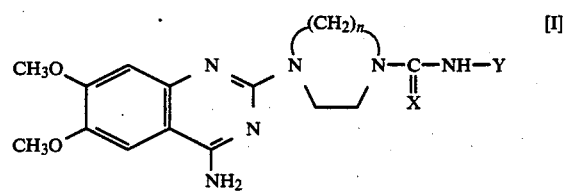

wherein Y represents a cycloalkyl group having 3 to 7 carbon atoms, a furyl group, a tetrahydrofuryl group, a tetrahydropyranyl group or a group of the formula:

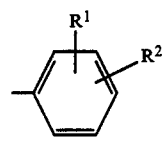

(in which $R^1$ and $R^2$ may be identical or different and each represent a hydrocarbon atom, a lower alkyl group having 1 to 5 carbon atoms, a lower alkoxy group having 1 to 5 carbon atoms, a halogen atom or a nitro group); X represents an oxygen atom or a sulfur atom; and n is an integer of 2 or 3.

In the above formula [I], the cycloalkyl group represented by the substituent Y may be exemplified by substituted or unsubstituted cyclopropyl group, cyclobutyl group, cyclopentyl group, cyclohexyl group and cycloheptyl group.

When the substituent Y is a group represented by the formula:

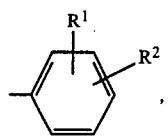

the lower alkyl represented by $R^1$ and $R^2$ having 1 to 5 carbon atoms is, for example, methyl, ethyl, propyl, iso-propyl, butyl, iso-butyl and pentyl. As the alkoxy group represented by $R^1$ and $R^2$, there may be mentioned methoxy, ethoxy, propoxy, iso-propoxy, butoxy, iso-butoxy and pentoxy. The halogen atom may include fluorine atom, chlorine atom and bromine atom.

As to the positions at which the substituents $R^1$ and $R^2$ are substituted on the phenyl group, $R^2$ may be substituted at 2-, 3- or 4-position when $R^1$ is a hydrogen atom,; or the phenyl group may be substituted at any combination of the positions, namely 2-position and 3- to 6-position or 3-position and 4- to 5-position, when $R^1$ and $R^2$ are both groups other than hydrogen atom.

Typical examples of the compounds according to the present invention represented by the formula [I] are set forth below.

| Compound No. | Name of Compound |
|---|---|
| 1 | 2-(4-cyclopropylcarbamoyl-piperazin-1-yl)-4-amino-6,7-dimethoxyquinazoline |
| 2 | 2-(4-cyclobutylcarbamoyl-piperazin-1-yl)-4-amino-6,7-dimethoxyquinazoline |
| 3 | 2-(4-cyclopentylcarbamoyl-piperazin-1-yl)-4-amino-6,7-dimethoxyquinazoline |
| 4 | 2-(4-cyclohexylcarbamoyl-piperazin-1-yl)-4-amino-6,7-dimethoxyquinazoline |
| 5 | 2-(4-cycloheptylcarbamoyl-piperazin-1-yl)-4-amino-6,7-dimethoxyquinazoline |
| 6 | 2-[4-(furan-2-yl)carbamoyl-piperazin-1-yl]-4-amino-6,7-dimethoxyquinazoline |
| 7 | 2-[4-(tetrahydrofuran-2-yl)carbamoyl-piperazin-1-yl]-4-amino-6,7-dimethoxyquinazoline |
| 8 | 2-[4-(tetrahydropyran-2-yl)carbamoyl-piperazin-1-yl]-4-amino-6,7-dimethoxyquinazoline |
| 9 | 2-(4-cyclohexylthiocarbamoyl-piperazin-1-yl)-4-amino-6,7-dimethoxyquinazoline |
| 10 | 2-(4-cyclohexylcarbamoyl-homopiperazin-1-yl)-4-amino-6,7-dimethoxyquinazoline |
| 11 | 2-(4-cyclohexylthiocarbamoyl-homopiperazin-1-yl)-4-amino-6,7-dimethoxyquinazoline |
| 12 | 2-(4-phenylcarbamoyl-piperazin-1-yl)-4-amino-6,7-dimethoxyquinazoline |
| 13 | 2-[4-(2-methylphenyl)carbamoyl-piperazin-1-yl]-4-amino-6,7-dimethoxyquinazoline |
| 14 | 2-[4-(3-methylphenyl)carbamoyl-piperazin-1-yl]-4-amino-6,7-dimethoxyquinazoline |
| 15 | 2-[4-(4-methylphenyl)carbamoyl-piperazin-1-yl]-4-amino-6,7-dimethoxyquinazoline |
| 16 | 2-[4-(4-isopropylphenyl)carbamoyl-piperazin-1-yl]-4-amino-6,7-dimethoxyquinazoline |
| 17 | 2-[4-(2-methoxyphenyl)carbamoyl-piperazin-1-yl]-4-amino-6,7-dimethoxyquinazoline |
| 18 | 2-[4-(3-methoxyphenyl)carbamoyl-piperazin-1-yl]-4-amino-6,7-dimethoxyquinazoline |
| 19 | 2-[4-(4-methoxyphenyl)carbamoyl-piperazin-1-yl]-4-amino-6,7-dimethoxyquinazoline |
| 20 | 2-[4-(2-ethoxyphenyl)carbamoyl-piperazin-1-yl]-4-amino-6,7-dimethoxyquinazoline |
| 21 | 2-[4-(4-ethoxyphenyl)carbamoyl-piperazin-1-yl]-4-amino-6,7-dimethoxyquinazoline |
| 22 | 2-[4-(2-n-propyloxyphenyl)carbamoyl-piperazin-1-yl]-4-amino-6,7-dimethoxyquinazoline |
| 23 | 2-[4-(4-n-propyloxyphenyl)carbamoyl-piperazin-1-yl]-4-amino-6,7-dimethoxyquinazoline |
| 24 | 2-[4-(butoxyphenyl)carbamoyl-piperazin-1-yl]-4-amino-6,7-dimethoxyquinazoline |
| 25 | 2-[4-(2-fluorophenyl)carbamoyl-piperazin-1-yl]-4-amino-6,7-dimethoxyquinazoline |
| 26 | 2-[4-(3-fluorophenyl)carbamoyl-piperazin-1-yl]-4-amino-6,7-dimethoxyquinazoline |
| 27 | 2-[4-(4-fluorophenyl)carbamoyl-piperazin-1-yl]-4-amino-6,7-dimethoxyquinazoline |
| 28 | 2-[4-(2-chlorophenyl)carbamoyl-piperazin-1-yl]-4-amino-6,7-dimethoxyquinazoline |
| 29 | 2-[4-(3-chlorophenyl)carbamoyl-piperazin-1-yl]-4-amino-6,7-dimethoxyquinazoline |
| 30 | 2-[4-(4-chlorophenyl)carbamoyl-piperazin-1-yl]-4-amino-6,7-dimethoxyquinazoline |
| 31 | 2-[4-(3,4-dichlorophenyl)carbamoyl-piperazin-1-yl]-4-amino-6,7-dimethoxyquinazoline |
| 32 | 2-[4-(4-bromophenyl)carbamoyl-piperazin-1-yl]-4-amino-6,7-dimethoxyquinazoline |
| 33 | 2-[4-(4-nitrophenyl)carbamoyl-piperazin-1-yl]-4-amino-6,7-dimethoxyquinazoline |
| 34 | 2-[4-(2-methyl-4-chlorophenyl)carbamoyl-piperazin-1-yl]-4-amino-6,7-dimethoxyquinazoline |
| 35 | 2-(4-phenylthiocarbamoyl-piperazin-1-yl)-4-amino-6,7-dimethoxyquinazoline |
| 36 | 2-[4-(4-nitrophenyl)thiocarbamoyl-piperazin-1-yl]-4-amino-6,7-dimethoxyquinazoline |
| 37 | 2-(4-phenylcarbamoyl-homopiperazin-1-yl)-4-amino-6,7-dimethoxyquinazoline |
| 38 | 2-(4-phenylthiocarbamoyl-homopiperazin-1-yl)-4-amino-6,7-dimethoxyquinazoline |

The compounds [I] of the present invention can be synthesized according to the route A or the route B as shown below:

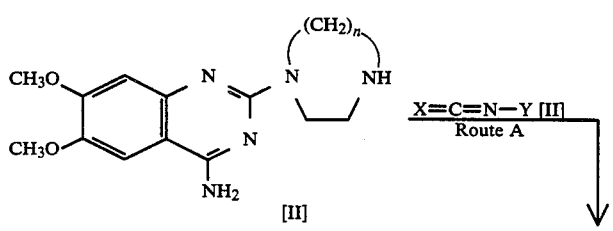

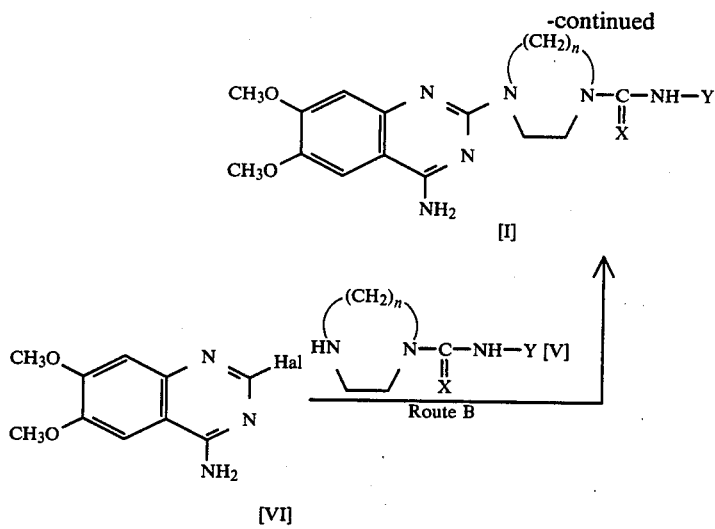

[I]

[VI]

In the above formulae [II] through [V], Hal represents a halogen atom, especially a chlorine atom or a bromine atom; Y, X and n have the same meanings as defined above.

According to the route A, the compound of the present invention [I] is produced by allowing the compound [II], namely 2-(piperazin-1-yl)-4-amino-6,7-dimethoxyquinazoline or 2-(homopiperazin-1-yl)-4-amino-6,7-dimethoxyquinazoline to react with the compound [III], namely isocyanate or isothiocyanate. The compound [II] and the method for preparation thereof are disclosed in U.S. Pat. No. 4,001,237 or Japanese Provisional Patent Publication No. 49(1974)-66690. The compound [III] is used in an amount of 0.5 to 1.5 equivalents, preferably 1 equivalent, based on the compound [II]. The reaction may be carried out in the absence of a solvent or in the presence of a solvent which does not interfere with the reaction. As the solvent, there may be employed aromatic hydrocarbons such as benzene, toluene, xylene, etc.; ethers such as ethyl ether, tetrahydrofuran, dioxane, etc.; ketones such as acetone, methyl ethyl ketone, etc.; ethyl acetate; dimethylformamide; dimethylacetamide; and dimethylsulfoxide. The reaction temperature may generally range from −20° to 100° C., preferably from 0° to 50° C. The reaction time may be generally from 30 minutes to 48 hours, preferably from 1 to 24 hours.

According to the route B, the compound of the present invention [I] is produced by allowing the compound [IV], namely 2-halogeno-4-amino-6,7-dimethoxyquinazoline, to react with the compound [V], namely substituted(thio)carbamoyl piperazine or substituted(thio)carbamoyl homopiperazine. The compound [IV] and the method for preparation thereof are disclosed in U.S. Pat. No. 3,511,836. The compound [V] can be prepared by reacting piperazine or homopiperazine, in which one of the nitrogen atoms is protected with a group such as a formyl group or a benzyl group, with isocyanate or thioisocyanate to obtain N-substituted-carbamoyl-N'-substituted-piperazine or N-substituted-carbamoyl-N'-substituted-homopiperazine in which one of the nitrogen atoms is protected, followed by removal of a protective group such as a formyl group or a benzyl group.

The reaction according to the route B may be conducted in the absence of a solvent or in the presence of a solvent which does not interfere with the reaction. As the solvent to be used in the reaction, there may included those as mentioned in the route A and also alcohols such as ethanol, propanol, isoamyl alcohol, and the like.

The reaction may be carried out at a temperature, generally in the range from 50° to 200° C., preferably from 70° to 150° C. The reaction time may be generally within the range from 0.5 to 24 hours, preferably from 1 to 8 hours. The compound [V] is used in an amount generally from 0.5 to 2.5 moles, preferably from 1 to 2 moles per mole of the compound [IV]. In order to permit the reaction to proceed smoothly, there may preferably be added an acid-acceptor such as triethylamine, N-methylmorpholine, pyridine, DBU(1,8-diaza-bicyclo[5,4,0]undecene-7), alkali bicarbonate, alkali carbonate, etc. or an excessive amount of the compound [V] to the reaction system.

The compound represented by the formula [I] prepared by a process as described above, namely 2-[4-substituted(thio)carbamoyl-piperazin-1-yl]-4-amino-6,7-dimethoxyquinazoline derivative or 2-[4-substituted(thio)carbamoyl-homopiperazin-1-yl]-4-amino-6,7-dimethoxyquinazoline derivative is obtained in the form of a free base or a pharmaceutically acceptable salt, depending on the preparation method employed. Conversion of a free base to such a salt or of such a salt to a free base may be effected according to conventional procedures.

The term "pharmaceutically acceptable acid addition salt" mentioned in the specification and claims means a salt which does not substantially increase the toxicity of a basic compound.

These salts encompass those with mineral acids such as hydrochloric acid, hydroiodic acid, hydrobromic acid, phosphoric acid, metaphosphoric acid, nitric acid and sulfuric acid as well as those with organic acids such as formic acid, acetic acid, propionic acid, phenylacetic acid, tartaric acid, citric acid, malic acid, benzoic acid, glycolic acid, gluconic acid, glucronic acid, gronic acid, succinic acid, lactic acid, ascorbic acid, fumaric acid, maleic acid, anthranylic acid, salicylic acid, methanesulfonic acid and arylsulfonic acid.

The pharmacological activities and toxicities of the compounds of the present invention are to be described hereinafter.

Antihypertensive test

Test samples were administered orally to spontaneously hypertensive rats (hereinafter abbreviated as "SHR") for measurement of antihypertensive activities.

Through a cannula chronically intubated into the abdominal aorta of a male SHR of 20 to 30 weeks after birth, mean blood pressure and heart rate were measured by means of an electronic recording system without anesthesia and restraint. Five rats were employed in one group of SHR. Each test sample was suspended in a 1% tragacanth solution and administered orally at a concentration adjusted so as to give a volume of 5 ml/kg. At 1, 3, 6 and 24 hours after administration of test samples, blood pressure and heart rate were determined.

Table 1 shows changes in blood pressure after administration of test samples. It can clearly been seen that the compounds of the present invention have sufficient and persistent antihypertensive activities.

As to the heart rate, there can be seen no significant change in both the exemplary compounds and prazosin as compared with reference group.

Acute toxic test

Ten ICR-strain male mice weighing from 25 to 35 g. were used per one group, after fasting for 6 hours (water was freely taken in). Each test sample was suspended in a 1% tragacanth solution and administered orally at a concentration adjusted so as to give a volume of 40 ml/kg. After administration, feed was given and observation was continued for one week. As comparative example, prazosin is shown.

Table 2 shows a $LD_{50}$ value of the exemplary compounds.

As apparently seen from the results of the pharmacological and toxic tests, the compounds of the present invention have excellent antihypertensive activities and low toxicities.

TABLE 1

Antihypertensive activities
(SHR 3 mg/kg, oral administration)

| Compound No. | Mean blood pressure before administration mmHg | Percent decrease in mean blood pressure after administration (%) | | | |
|---|---|---|---|---|---|
| | | 1 hr | 3 hrs | 6 hrs | 24 hrs |
| 3 | 177 | −27.1 | −27.0 | −27.0 | −0.3 |
| 4 | 183 | −26.8 | −26.2 | −25.1 | −4.9 |
| 5 | 182 | −18.4 | −24.7 | −19.2 | −3.7 |
| 6 | 193 | −11.9 | −14.5 | −11.4 | +1.0 |
| 9 | 176 | −19.3 | −22.2 | −20.5 | −1.3 |
| 12 | 188 | −13.3 | −19.7 | −17.0 | 3.7 |
| 13 | 173 | −20.2 | −17.9 | −21.4 | 1.2 |
| 15 | 179 | −17.1 | −18.5 | −21.8 | 1.2 |
| 18 | 169 | −5.9 | −17.2 | −15.9 | 4.6 |
| 21 | 187 | −22.4 | −24.5 | −27.7 | −6.4 |
| 25 | 182 | −30.3 | −22.0 | −23.8 | −7.3 |
| 26 | 192 | −21.5 | −21.7 | −24.3 | 0 |
| 29 | 183 | −15.1 | −18.5 | −19.4 | −4.9 |
| 34 | 182 | −12.1 | −19.0 | −18.2 | −1.2 |
| 35 | 186 | −28.0 | −20.9 | −24.7 | 0.6 |
| 37 | 170 | −11.7 | −12.8 | −5.0 | 0 |
| Prazosin (Comparative example) | 179 | −27.9 | −17.3 | −19.0 | −1.7 |

TABLE 2

| Compound No. | Acute toxicity in mice | | $LD_{50}$ (mg/kg, oral) |
|---|---|---|---|
| | Dosage (mg/kg, oral) | Number of dead mouse | |
| 3 | 2,500 | 0 | >5,000 |
| | 5,000 | 0 | |
| 4 | 2,500 | 0 | >5,000 |
| | 5,000 | 0 | |
| 12 | 2,500 | 0 | >5,000 |
| | 5,000 | 0 | |
| 13 | 2,500 | 5 | 2,500 |
| | 5,000 | 10 | |
| 21 | 2,500 | 0 | >5,000 |
| | 5,000 | 0 | |
| 25 | 1,250 | 3 | 1,870 |
| | 2,500 | 7 | |
| | 5,000 | 10 | |
| 35 | 2,500 | 0 | >5,000 |
| | 5,000 | 0 | |
| Prazosin (Comparative example) | 2,500 | 0 | >5,000 |
| | 5,000 | 0 | |

(Ten mice/group)

The compounds of the present invention are useful for prevention and therapy of various hypertensions such as essential hypertension, renal hypertension, adrenal hypertension and malignant hypertension.

The compounds of the present invention can be administered in various forms, orally in the form of powders, fine granules, granules, tablets, pills, capsules, solutions and suspensions, or non-orally in the form of injections and suppositories, etc.

The compounds of the present invention can be administered at a dose, which should adequately be selected depending on the state of diseases to be treated and may be generally within the range from 0.1 to 200 mg/day, preferably from 1 to 50 mg/day, by oral administration, for an adult. These compounds can be administered to hypertensive patients either simply or in combination with pharmaceutically acceptable carrier.

The ratio of the active ingredients to carriers may conveniently be determined in view of solubility and chemical properties of the compound employed, the route selected from administration as well as the standard manufacturing processes. For example, they can be administered in the form of tablets using excipients such as lactose, crystalline cellulose, calcium carbonate and dibasic calcium phosphate. There may also frequently be used various disintegrating agents such as starch, calcium carboxymethylcellulose, and certain species of silicates togehter with lubricant such as magnesium stearate, calcium stearate and talc. For capsules to be orally administered, lactose and crystalline cellulose are preferred. When an aqueous suspension is desirable, the active ingredients are blended with emulsifiers and/or suspension agents. There may also be employed a combination with a diluent such as ethanol, propylene glycol and glycerine.

For non-oral administration, there may be employed a solution of the active ingredients mixed with other solutes such as glucose or salts. Such solutions should adequately be buffered to be made isotonic, if desired. In case of suppositories, there may be employed Witepsol, cacao butter and polyethylene glycol.

The dosage required for decreasing the blood pressure of a hypertensive patient may be determined depending on the characteristic and the extent of the hypertension. Generally speaking, there is at first applied a small dosage, and then the dosage is gradually increased until the optimum level can be determined. When a preparation is orally administered, it is generally required to use a greater dosage of active ingredients in order to obtain the same extent of antihypertensive effects as obtained by non-oral administration.

The present invention is further illustrated with reference to Reference Examples and Examples, by which the present invention is not limited.

EXAMPLE 1

Synthesis of 2-(4-cyclopentylcarbamoyl-piperazin-1-yl)-4-amino-6,7-dimethoxyquinazoline (Compound No. 3)

In 30 ml of dioxane, there was dissolved 1.16 g. (4 mmole) of 2-piperazino-4-amino-6,7-dimethoxyquinazoline. To the resultant solution was added dropwise 0.45 g. (4 mmole) of cyclopentyl isocyanate at room temperature and the mixture was stirred overnight at room temperature. The precipitated crystals were recovered by filtration to obtain 1.34 g. of the desired product.
Yield: 83.6%,
m.p.: 200°–202° C. (recrystallized from iso-propanol),
IR(cm$^{-1}$): 1625, 1565.

EXAMPLES 2–6

In place of cyclopentyl isocyanate employed in Example 1, there were employed the isocyanates as indicated in the following Table 3. Example 1 was repeated under otherwise the same conditions to synthesize various 2-(4-substitutedcarbamoyl-piperazin-1-yl)-4-amino-6,7-dimethoxyquinazolines as shown in the Table 3 below.

IR(cm$^{-1}$): 1630, 1595.

EXAMPLE 8

Synthesis of 2-(4-cyclohexylcarbamoyl-homopiperazin-1-yl)-4-amino-6,7-dimethoxyquinazoline (Compound No. 10)

A solution prepared by dissolving 479 mg. (2 mmole) of 2-chloro-4-amino-6,7-dimethoxyquinazoline and 451 mg. (2 mmole) of N-cyclohexylcarbamoyl-homopiperazine (oily substance, showing IR absorption spectrum at 3340, 2920, 1630 cm$^{-1}$) in 10 ml of isoamyl alcohol was refluxed for 4 hours, followed by standing overnight. The precipitates were collected by filtration to obtain 310 mg. of the desired hydrochloride.
Yield: 33.3%,
m.p.: 290° C. (decompd.),
IR(cm$^{-1}$): 1630, 1590.

EXAMPLE 9

Synthesis of 2-(4-phenylcarbamoyl-piperazin-1-yl)-4-amino-6,7-dimethoxyquinazoline (Compound No. 12)

To a solution prepared by dissolving 1.16 g. (4 mmole) of 2-piperazino-4-6,7-dimethoxyquinazoline in 30 ml of dioxane, there was added dropwise a solution of 0.48 g. (4 mmole) of phenyl isocyanate dissolved in 10 ml of dioxane. The mixture was further continued to be stirred overnight. After evaporation of the solvent, the residue was chromatographed on silica gel and eluted with 20% dioxane-chloroform to obtan 1.19 g. of the desired product.
Yield: 72.9%,
m.p.: 137°–139° C. (recrystallized from ethanol-

TABLE 3

| Example No. | Compound [III] | Product Compound No. | X | R | Yield (%) | m.p. (°C.) | IR (cm$^{-1}$) |
|---|---|---|---|---|---|---|---|
| 2 | cyclopropyl isocyanate | 1 | 0 | cyclopropyl | 23.5 | 255–260 (decompd.) | 1620, 1565 |
| 3 | cyclohexyl isocyanate | 4 | 0 | cyclohexyl | 77.4 | 177–179 (decompd.) | 1615, 1565 |
| 4 | cycloheptyl isocyanate | 5 | 0 | cycloheptyl | 79.3 | 144–147 (decompd.) | 1620, 1565 |
| 5 | furan-2-yl isocyanate | 6 | 0 | 2-furyl | 45.4 | (hydrochloride) 230–240 (decompd.) | 1630, 1565 |
| 6 | tetrahydrofuran-2-yl isocyanate | 7 | 0 | 2-tetrahydrofuryl | 83.9 | 181–183 | 1625, 1560 |

EXAMPLE 7

Synthesis of 2-(4-cyclohexylthiocarbamoyl-piperazin-1-yl)-4-amino-6,7-dimethoxyquinazoline (Compound No. 9)

To a solution prepared by dissolving 868 mg. (3 mmole) of 2-piperazine-4-amino-6,7-dimethoxyquinazoline in 30 ml of dioxane, there was added dropwise 424 mg. (13 mmole) of cyclopentyl isothiocyanate at room temperature. The mixture was stirred overnight at room temperature. After evaporation of the solvent from the reaction mixture, the residue was chromatographed on silica gel, and eluted with 2% ethanol-chloroform to obtain 1.26 g. of the desired product. The product was dissolved in 10 ml of iso-propanol and 2 ml of 2N hydrochloric acid was added to the resultant solution to form a hydrochloride, which was in turn isolated.
Yield: 1.21 g. (86.3;1 %),
m.p.: 195°–197° C.

water),
IR(cm$^{-1}$): 1630, 1585, 1570.

EXAMPLE 10

Synthesis of 2-[4-(2-fluorophenyl)-carbamoyl-piperazin-1-yl]-4-amino-6,7-dimethoxyquinazoline (Compound No. 25)

In 30 ml of dioxane, there was dissolved 1.16 g. (4 mmole) of 2-piperazino-4-amino-6,7-dimethoxyquinazoline. To the resultant solution was added dropwise a solution of 0.55 g. (4 mmole) of 2-fluorophenylisocyanate dissolved in 10 ml of dioxane, followed further by stirring overnight. After evaporation of the solvent, the residue was chromatographed on silica gel and eluted with 5% ethanol-chloroform to obtain 1.22 g. of an oily product (Yield: 71.5%). The oily product was dissolved in 5 ml of ethanol and 2N hydrochloric acid was added to the solution under ice-cooling. The precipitates were collected by filtration to obtain 0.89 g. of the desired product as hydrochloride.

m.p.: about 250° C. (decompd.)

Elemental analysis: for $C_{21}H_{23}F_1N_6O_3 \cdot HCl \cdot H_2O$

|  | C | H | N |
|---|---|---|---|
| Calculated: | 52.45 | 5.45 | 17.47 |
| Found: | 52.42 | 5.34 | 17.42 |

IR(cm$^{-1}$): 1630, 1590.

EXAMPLES 11-25

Synthesis of
2-(4-substituted-phenylcarbamoyl)-piperazin-1-yl)-4-amino-6,7-dimethoxyquinazoline (X=O).

Example 9 was repeated by using corresponding substituted phenylisocyanate in place of phenylisocyanate used in Example 9 to prepare the compounds of the present invention. Conversion of the product to hydrochloride was performed in the same manner as in Example 10.

The results are shown in Table 4.

TABLE 4

| Example No. | Compound No. | Substituents on phenyl R$^1$ | R$^2$ | Yield (%) | m.p. (°C.) | IR (cm$^{-1}$) |
|---|---|---|---|---|---|---|
| 11 | 13 | 2-methyl | Hydrogen atom(H) | 73.4 | 242–247 (hydrochloride) | 1630, 1595 |
| 12 | 15 | 4-methyl | H | 46.6 | 213–216 (hydrochloride) | 1630, 1595 |
| 13 | 16 | 4-iso-propyl | H | 66.6 | 254–258 | 1620, 1580 |
| 14 | 18 | 3-methoxy | H | 45.6 | 198–199 (hydrochloride) | 1630, 1595 |
| 15 | 20 | 2-ethoxy | H | 42.6 | 255–259 (hydrochloride) | 1630, 1595 |
| 16 | 21 | 4-ethoxy | H | 75.1 | 160–165 | 1620, 1580 |
| 17 | 22 | 4-n-propyloxy | H | 49.0 | 183–186 | 1625, 1565 |
| 18 | 26 | 3-fluoro | H | 68.6 | 195–200 (hydrochloride) | 1630, 1590 |
| 19 | 27 | 4-fluoro | H | 74.9 | 235–239 | 1630, 1595 |
| 20 | 28 | 2-chloro | H | 88.7 | 190–193 (hydrochloride) | 1630, 1595 |
| 21 | 29 | 3-chloro | H | 65.7 | 206–209 (hydrochloride) | 1630, 1590 |
| 22 | 30 | 4-chloro | H | 47.7 | 146–147 | 1625, 1580, 1560 |
| 23 | 31 | 3-chloro | 4-chloro | 53.1 | 131–134 | 1625, 1585 |
| 24 | 32 | 4-bromo | H | 53.0 | 224–227 (hydrochloride) | 1645, 1625, 1590 |
| 25 | 34 | 2-methyl | 4-chloro | 36.5 | 149–151 | 1630, 1580, 1565 |

EXAMPLE 26

Synthesis of
2-(4-phenylthiocarbamoyl-piperazin-1-yl)-4-amino-6,7-dimethoxyquinazoline (Compound No. 35)

In 20 ml of dioxane, there was dissolved 0.87 g. (3 mmole) of 2-piperazino-4-amino-6,7-dimethoxyquinazoline. To the resultant solution was added dropwise a solution of 0.41 g. (3 mmole) of phenylisothiocyanate dissolved in 10 ml of dioxane at room temperature. The mixture was further stirred overnight. After evaporation of the solvent, the residue was chromatographed on silica gel and eluted with 20% dioxane-chloroform to obtain 0.89 g. of the desired product.

Yield: 69.9%, m.p.: 138°–140° C. (recrystallized from ethanol)

IR(cm$^{-1}$): 1630, 1580, 1560.

EXAMPLE 27

Synthesis of
2-[4-(4-nitrophenyl)-thiocarbamoylpiperazin-1-yl]-4-amino-6,7-dimethoxyquinazoline (Compound No. 36)

A solution of 0.72 g. (4 mmole) of 4-nitrophenyl-isothiocyanate dissolved in 10 ml of dioxane was added dropwise at room temperature to a solution which had been prepared by dissolving 1.16 g. (4 mmole) of 2-piperazino-4-amino-6,7-dimethoxyquinazoline in 30 ml of dioxane. The mixture was further subjected to stirring overnight. The precipitated crystals were collected by filtration to obtain 1.30 g. of the desired product.

Yield: 69.2%, m.p.: 178°–180° C. (decompd.) (recrystallized from dimethyl sulfoxideethanol), IR(cm$^{-1}$): 1630, 1570.

Reference Example

Synthesis of N-(4-methoxyphenylcarbamoyl)piperazine

To a solution prepared by dissolving 3.53 g. (20 mmole) of benzylpiperazine in 30 ml of chloroform, there was added dropwise a solution of 2.66 g. (20 mmole) of 4-methoxyphenyl isocyanate dissolved in 5 ml of chloroform at room temperature. The mixture was continued to be stirred overnight and thereafter the solvent was evaporated under reduced pressure. The residue was recrystallized from ethanol to give 5.02 g. of N-benzyl-N'-(4-methoxyphenylcarbamoyl)piperazine.

Yield: 77.1%, m.p.: 164°–165° C.

Suspension of 3.25 g. (10 mmole) of N-benzyl-N'-(4-methoxyphenylcarbamoyl)piperazine and 0.10 g. of 5%-palladium-carbon was stirred under hydrogen at 60° C. for 7 hours. After the catalyst was filtered off, ethanol was evaporated under reduced pressure to give 1.92 g. of the desired product as oily substance.

Yield: 81.7%,

Decomposition temperature of the hydrochloride: 258°–262° C.

EXAMPLE 28

Synthesis of
2-[4-(4-methoxyphenyl)carbamoyl-piperazin-1-yl]-4-amino-6,7-dimethoxyquinazolone (Compound No. 19)

A mixture of 479 mg. (2 mmole) of 2-chloro-4-amino-6,7-dimethoxyquinazoline and 471 mg. (2 mmole) of N-(4-methoxycarbamoyl)piperazine in 20 ml of isoamyl alcohol was refluxed for 4 hours. After the reaction mixture was cooled, the precipitates were collected by filtration to obtain 0.65 g. of the desired product in the form of hydrochloride.

Yield: 68.4%,
m.p.: 262°–267° C. (decompd.),
IR(cm$^{-1}$): 1630, 1590.

EXAMPLE 29

Synthesis of 2-(4-phenylcarbamoyl-homopiperazin-1-yl)-4-amino-6,7-dimethoxyquinazoline (Compound No. 37)

To a solution of 1.21 g. (4 mmole) of 2-homopiperazino-4-amino-6,7-dimethoxyquinazoline in 30 ml of dioxane, there was added dropwise a solution of 0.48 g. (4 mmole) of phenyl isocyanate in 10 ml of dioxane at room temperature, followed further by stirring overnight. After evaporation of the solvent, the residue was dissolved in 10 ml of ethanol. While the resultant solution was subjected to ice-cooling, 2 ml of 2N-hydrochloric acid was added thereto. The precipitates were collected by filtration to obtain 0.89 g. of the desired product in the form of hydrochloride.

Yield: 48.5%,
m.p.: 260°–265° C.
IR(cm$^{-1}$): 1630, 1590.

We claim:

1. A quinazoline derivative represented by the following formula [I] or a pharmaceutically acceptable acid addition salt thereof:

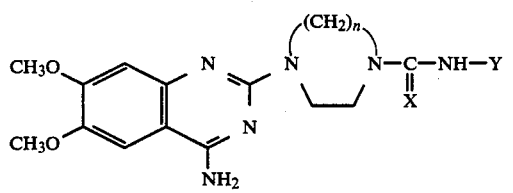

wherein Y represents a cycloalkyl group having 5 to 7 carbon atoms, a furyl group, or a group of the formula:

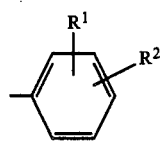

in which $R^1$ and $R^2$ are identical or different and each represent a hydrogen atom, a lower alkyl group having 1 to 5 carbon atoms, a lower alkoxy group having 1 to 5 carbon atoms, a halogen atom or a nitro group, X represents an oxygen atom or a sulfur atom; and n is 2.

2. The quinazoline derivative claimed in claim 1, wherein Y represents said cycloalkyl group having 5 to 7 carbon atoms.

3. The quinazoline derivative claimed in claim 1, wherein Y represents said group of the formula

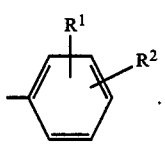

4. The antihypertensive pharmaceutical compositions claimed in claim 2, wherein said antihypertensive effective amount is within the range from 0.1 to 200 mg/day.

5. The quinazoline derivative of claim 1 which is 2-(4-cyclopentylcarbamoyl-piperazin-1-yl)-4-amino-6,7-dimethoxyquinazoline.

6. The quinazoline derivative of claim 1 which is 2-(4-cyclohexylcarbamoyl-piperazin-1-yl)-4-amino-6,7-dimethoxyquinazolone.

7. The quinazoline derivative of claim 1 which is 2-(4-cycloheptylcarbamoyl-piperazin-1-yl)-4-amino-6,7-dimethoxyquinazolone.

8. The quinazoline derivative of claim 1 which is 2-[4-(furan-2-yl)carbamoyl-piperazin-1-yl]-4-amino-6,7-dimethoxyquinazolone.

9. The quinazoline derivative of claim 1 which is 2-(4-cyclohexylthiocarbamoyl-piperazin-1-yl)-4-amino-6,7-dimethoxyquinazoline.

10. The quinazoline derivative of claim 1 which is 2-(4-phenylcarbamoyl-piperazin-1-yl)-4-amino-6,7-dimethoxyquinazoline.

11. The quinazoline derivative of claim 1 which is 2-[4-(2-methylphenyl)carbamoyl-piperazin-1-yl]-4-amino-6,7-dimethoxyquinazoline.

12. The quinazoline derivative of claim 1 which is 2-[4-(4-methylphenyl)carbamoyl-piperazin-1-yl]-4-amino-6,7-dimethoxyquinazoline.

13. The quinazoline derivative of claim 1 which is 2-[4-(3-methoxyphenyl)carbamoyl-piperazin-1-yl]-4-amino-6,7-dimethoxyquinazoline.

14. The quinazoline derivative of claim 1 which is 2-[4-(4-ethoxyphenyl)carbamoyl-piperazin-1-yl]-4-amino-6,7-dimethoxyquinazoline.

15. The quinazoline derivative of claim 1 which is 2-[4-(2-fluorophenyl)carbamoyl-piperazin-1-yl]-4-amino-6,7-dimethoxyquinazoline.

16. The quinazoline derivative of claim 1 which is 2-[4-(3-fluorophenyl)carbamoyl-piperazin-1-yl]-4-amino-6,7-dimethoxyquinazoline.

17. The quinazoline derivative of claim 1 which is 2-[4-(3-chlorophenyl)carbamoyl-piperazin-1-yl]-4amino-6,7-dimethoxyquinazoline.

18. The quinazoline derivative of claim 1 which is 2-[4-(2-methyl-4-chlorophenyl)carbamoyl-piperazin-1-yl]-4-amino-6,7-dimethoxyquinazoline.

19. The quinazoline derivative of claim 1 which is 2-(2-phenylthiocarbamoyl-piperazin-1-yl)-4-amino-6,7-dimethoxyquinazoline.

20. The quinazoline derivative of claim 1 which is 2-[4-(4-fluorophenyl)carbamoyl-piperazin-1-yl]-4-amino-6,7-dimethoxyquinazoline.

21. The quinazoline derivative of claim 1 which is 2-[4-(3,4-dichlorophenyl)carbamoyl-piperazin-1-yl]-4-amino-6,7-dimethoxyquinazoline.

22. An antihypertensive composition, comprising an antihypertensive effective amount of a quinazoline derivative represented by the following formula or a pharmaceutically acceptable acid addition salt thereof:

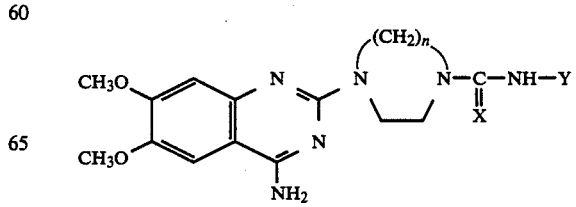

wherein Y represents a cycloalkyl group having 5 to 7 carbon atoms, a furyl group, or a group of the formula:

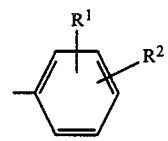

in which $R^1$ and $R^2$ are identical or different and each represent a hydrogen atom, a lower alkyl group having 1 to 5 carbon atoms, a lower alkoxy group having 1 to 5 carbon atoms, a halogen atom or a nitro group; X represents an oxygen atom or a sulfur atom; and n is 2 combined with a pharmaceutically acceptable carrier.

* * * * *